United States Patent [19]
Andruski et al.

[11] Patent Number: 5,177,242
[45] Date of Patent: Jan. 5, 1993

[54] PROCESS FOR PREPARING OPTICALLY ACTIVE CYANOHYDRINS WITH ENZYMES

[75] Inventors: Stephen W. Andruski, Hightstown; Bruce Goldberg, Clifton, both of N.J.

[73] Assignee: FMC Corporation, Philadelphia, Pa.

[21] Appl. No.: 809,803

[22] Filed: Dec. 17, 1991

[51] Int. Cl.⁵ .................. C07C 253/16; C07C 253/30
[52] U.S. Cl. ..................................... 558/351; 435/128
[58] Field of Search ......................... 558/351; 435/128

[56] References Cited

U.S. PATENT DOCUMENTS

| | | | |
|---|---|---|---|
| 3,862,030 | 1/1975 | Goldberg | 210/24 |
| 4,102,746 | 7/1978 | Goldberg | 195/63 |
| 4,169,014 | 9/1979 | Goldberg | 435/182 |
| 4,859,784 | 8/1989 | Effenberger et al. | 549/491 |
| 4,900,667 | 2/1990 | Arena | 558/351 X |
| 4,959,467 | 9/1990 | Arena | 558/351 X |
| 5,008,192 | 4/1991 | Neidermeyer et al. | 435/128 |
| 5,122,462 | 6/1992 | Miethe et al. | 435/128 |

FOREIGN PATENT DOCUMENTS

| | | |
|---|---|---|
| 3810489 | 1/1990 | Australia |
| 0326063 | 8/1989 | European Pat. Off. |
| 350908 | 1/1990 | European Pat. Off. |
| 3823864 | 8/1989 | Fed. Rep. of Germany |

OTHER PUBLICATIONS

"A Novel Immobilized Enzyme Reactor System" Goldberg, AICHE Symposium (May 10, 1984).

"Continuous (R)-mandelic acid production in an enzyme membrane reactor", Vasic-Racki et al., *Appl. Microbial Biotechnol.*, 31, pp. 215-222 (1989).

"Engineering Aspects of Enzyme Engineering" Kragl. et al., *Annals New York Academy of Sciences*, pp. 167-175 (1990).

*Primary Examiner*—Joseph P. Brust
*Attorney, Agent, or Firm*—Stanford M. Back; Robert M. Kennedy

[57] ABSTRACT

The reaction time and ease of handling of reactants in the known process of forming optically active (S)-cyanohydrins by reacting aldehydes with hydrocyanic acid in the presence of the enzyme S-oxynitrilase and a solvent may be significantly improved over the known methods when the solution of aldehydes and acid is passed through a porous membrane comprising a polymeric resinous binder having finely divided filler particles dispersed throughout the binder to which the S-oxynitrilase enzyme has been chemically bound.

11 Claims, No Drawings

PROCESS FOR PREPARING OPTICALLY ACTIVE CYANOHYDRINS WITH ENZYMES

BACKGROUND OF THE INVENTION

1. Field of the Invention

This invention relates to a process for the preparation of cyanohydrins. More particularly, it relates to an improved process for the preparation of optically active (S)-cyanohydrins, useful as intermediates in the preparation of known pyrethroid insecticides, comprising reacting aldehydes with hydrocyanic acid in the presence of S-oxynitrilase enzyme.

2. Statement of Related Art

The process of reacting aldehydes with hydrocyanic acid in the presence of the enzyme oxynitrilase and the solvent diisopropyl ether to form optically active cyanohydrins is known, for example, from U.S. Pat. No. 4,859,784 to Effenberger et. al., which is incorporated herein by reference. As taught by this reference, the reaction is carried out with the enzyme in an immobilized form, such as bound to the surface of glass spheres, ion-exchange resins, or particles of cellulose, in the form of a slurry which must first be filtered out of solution before the product can be recovered. While effective for the purpose intended, this method is characterized by only a single pass of reactants through the immobilized enzyme, which pass-through takes 5 to 6 days to complete. Similarly, Australian Patent Application 38104/89, to Kula et. al., teaches a like process in which the enzyme, S-oxynitrilase, is derived from a particular source (*Sorohum bicolor*). In this process, there is used in one embodiment, an acrylic bead to immobilize the enzyme, i.e., Eupergit ® C (Rohm, Darmstadt), a commercially available acrylic bead which is useful suspended in the reaction medium or in a column. In either event, it must be used only in an aqueous system to avoid any attack on the acrylic bead by various organic solvents. Moreover, in this latter process employing bound enzymes, a yield of about 85 wt. % is obtained, but only after a 3-day continuous run, using as the aldehyde 4-hydroxybenzaldehyde. See also U.S. Pat. No. 5,008,192 to Neidermeyer; European Patent 326,063; U.S. Pat. No. 3,862,030; and German Offen. 3823864 A-1, which are cumulative to or correspond to the above U.S. and Australian references.

In each of the above patents, reference is made to an "enzyme-diaphragm-reactor." However, as the corresponding technical literature reveals, (see, for example, "Engineering Aspects of Enzyme Engineering," and footnotes 16 and 17 therein, i.e., Kragel et al., *Ann. N.Y. Aca. Sci.*, 613, pp. 167–175, (1990), and Vasic-Racki et. al., *Appl. Microbiol. Biotechnol.* 31, pp. 215–222 (1989)), such reactors represent nothing more than a series of containers separated by filtration membranes to which the enzyme is physically impervious. Thus, in this type of reactor the reaction is carried out in a solution containing a dispersed enzyme with which the reactants must then eventually come in contact by diffusion.

The use of polymeric membrane reactors to bind enzymes is generally known from U.S. Pat. Nos. 4,102,746, and 4,169,014, both to Bruce S. Goldberg. See also, "A Novel Immobilized Enzyme Reactor System," Bruce S. Goldberg, presented at the 27th Annual Spring Symposium Session on Non-Conventional Reactor Systems, AICHE, East Brunswick, N.J., May 10, 1984, which further describes the membrane reactors of these two U.S. patents. These latter two patents and the AICHE presentation of May 10, 1984 are also incorporated herein by reference.

SUMMARY OF THE INVENTION

It has now been found that, in accordance with the present invention, the reaction time and ease of handling of reactants in the otherwise known process of forming optically active (S)-cyanohydrins by reacting aldehydes with hydrocyanic acid in the presence of the catalytic enzyme S-oxynitrilase and a solvent, may be significantly improved over the aforedescribed methods when the solution of aldehyde and acid is passed through a chemically activated porous membrane as defined below to which the S-oxynitrilase enzyme has been chemically bound.

That is to say, whereas the (S)- and (R)-enantiomeric forms of the cyanohydrin would normally be formed in equal amounts, i.e. in ratios of 50:50, absent an stereoselective catalyst, it is an object of this invention to increase the ratio of the (S)-isomer over the (R)-isomer ("S/R"), by the proper selection of improved catalyst and reaction conditions. It is a further object of this invention to not only increase the selectivity of the S- to R-isomers, but also to provide a high conversion to product, and in as short a time as possible. It is yet another object to attain these ends without having to physically separate the enzyme from the final product.

DETAILED DESCRIPTION

The process of this invention of preparing the desired optically active cyanohydrins is readily carried out as described above, i.e. by passing a solution of aldehyde and hydrocyanic acid through a defined porous membrane to which the enzyme has been chemically bound, either in a batch or continuous manner, for a selected period of time, and recovering the desired optically active cyanohydrin. When thus carried out, it has been found that surprisingly the reaction time may be reduced to as little as one day, as contrasted with prior methods taking up to 6 or 7 days, while at the same time maintaining, or in some cases, increasing the overall yield of product as well as the selectivity for the desired S-isomer, when compared to these earlier methods. Conversely, and more preferably, it will be understood that by this method the overall yield can be multiplied proportionally when the prior art time periods of several days are utilized, e.g. up to 6 to 7 days.

Desirably, the reaction should be carried out in an organic system in which the substantially water-insoluble aldehyde, and resulting cyanohydrin, are soluble. While small amounts of an aqueous buffer, i.e. up to about 1 wt. % of water, based on the total weight of the system, may be used, it is preferred that as little water as possible be employed, i.e., about ≦0.03%. Thus, this invention essentially comprises a system consisting of an organic solvent (optionally containing an aqueous buffer), the aldehyde and acid reactants, and an enzyme chemically bound to a defined porous membrane, as described in detail below.

The reaction may be conducted under a wide range of temperatures and pH conditions which are not critical.

Thus, for example, temperatures of from about −6° C. to +30° C., preferably about +6° C. to +25° C., are acceptable. The pH conditions, while not critical, may be controlled by such buffer systems as sodium acetate, sodium citrate, or sodium phosphate, and may range from a pH of about 3.5 to 7.5.

The aldehydes employed are those conventionally taught, for example, in U.S. Pat. No. 4,859,784 (above), all of which, are incorporated herein by reference. Included therein, as described in this patent, are aldehydes of the formula

wherein R may be saturated or unsaturated, aliphatic or aromatic, and which may be substituted by halogen, sulfur-, nitrogen-, or oxygen-containing substituents.

The aldehydes selected for this process should desirably be substantially water-insoluble, i.e., they should be preferentially soluble in the organic solvents of this invention. Thus, aldehydes having solubility in water of less than about 2.0-0.01 mg/ml are preferred, and most preferably those having solubilities of less than 0.1 mg/ml, down to about 0.01 mg/ml. Examples of these water-insoluble aldehydes include those represented by the formula

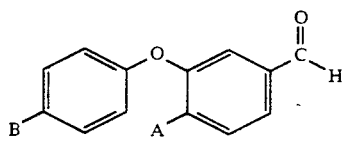

wherein A is hydrogen or fluorine; and B is hydrogen, fluorine, chlorine or bromine. Of these, 3-phenoxybenzaldehyde is preferred.

The molar ratio of aldehyde to hydrocyanic acid is desirably from about 1:1 to 1:100, and more preferably from about 1:1 to 1:2.

The nature of the organic solvent employed may be readily selected from those which do not adversely affect the membrane employed or the nature of the reaction. Thus, for example, the use of di-n-butyl ether, on the one hand, is preferred, while di-isopropyl ether, which is used in the process of U.S. Pat. No. 4,859,784 (above), has been found unexpectedly to render the present process inoperative.

The S-oxynitrilase enzyme catalyst (EC 4.1.2.11) is commercially available from Sigma Chemical Co., or may be isolated from sorghum shoots by known methods (see Bove et al., *J. Biol. Chem.*, 226 (1), 207, (1961)). The amount of enzyme employed relative to the aldehyde is desirably about 50-2500 units of enzyme per gram of aldehyde, more preferably about 500-750 units per gram of aldehyde. The enzyme may conveniently be chemically bound to the porous membrane described below by treatment of the membrane with, e.g., a 5 wt. % aqueous solution of polyethyleneimine, followed by, e.g., a 5 wt. % aqueous solution of glutaraldehyde and finally, a solution of S-oxynitrilase enzyme in an appropriate buffer.

Advantageously, the enzyme remains affixed to the membrane for several days at a time, and thus not only represents a more stable and durable arrangement compared to the prior art methods, but also there is avoided the extra step of separation and recovery of the enzyme which is in slurry form in the U.S. Pat. No. 4,859,784 and the U.S. Pat. No. 5,008,192.

The porous membranes used herein are described fully in U.S. Pat. No. 4,102,746 (above), which defines these enzyme-binding materials, the nature and method for preparing the same, and the affixing and recovery of the enzymes on a variety of such materials. Basically, these membranes, of a selected thickness, and/or layers, are comprised of an insoluble, three-dimensional polymeric resinous binder having finely divided filler particles dispersed throughout said binder and a network of substantially interconnected pores therein, wherein the pore size may vary widely, most desirably from about 0.01 to about 100 microns, and the total porosity of the material is about 50 to 75%, and said dispersed filler particles being present in an amount of at least about 25% by weight based on the total weight of the composition.

One such membrane is an MPS ® membrane (FMC Corporation, Philadelphia, Pa., U.S.A.), which is a microporous poly(vinyl chloride)-silica sheet with a porosity volume in the 70-80% range. The pore size, as determined by Mercury Intrusion Porosimetry, is generally in the 0.2 $\mu$m to 2.0 $\mu$m range. This support is extremely hydrophilic, has a negative charge that can be changed to positive, and a surface area of 80m$^2$/g. Also, this material is non-compressible under normal conditions and has a low dry density of 0.45 g/cm$^3$. The active sites are on the silica contained within the porous matrix which allows the addition of organic functionality via silica attachment chemistries. This MPS membrane has a DNA binding capacity of at least about 260 $\mu$g/cm$^2$. Moreover, it has been found that this membrane, as well as other suitable membranes which may be employed herein, while normally employed only in aqueous environments, is surprisingly stable under the organic solvent conditions of this process.

While the polymers which form the binder, i.e., the matrix, of the membrane may vary widely, they are desirably thermoplastic, commercially available resins of which poly(vinyl chloride) (PVC) is preferred. However, there may also be employed such materials as polyethylene filled with silica, or copolymers of PVC with small amounts of monoethylenic monomers such as vinyl acetate, vinylidene chloride, propylene, or the like. Alternatively, the matrix may be formed from such materials as polytetrafluoroethylene (PTFE), cellulose acetate or triacetate, polyamides, (such as nylon), or the like. The PTFE, if employed, may be in the form of a fibril matrix (see U.S. Pat. Nos. 4,152,661 and 4,373,519), having, for example, hydrophilic absorptive particles incorporated therein. Thus, in general, any thermoplastic resin which is readily plasticized by a solvent, or is sinterable by heat or pressure, or which can be readily formed starting with a pervious matrix, and which is chemically and physically stable under the conditions of this invention may be so employed.

Fillers, preferably in particulate form, may include both inorganic materials, such as the aforementioned silica compounds, or, e.g., aluminum compounds such as aluminum oxide or hydroxide; or organic fillers, such as polysaccharides, including activated cellulose derivatives. (Non-activated cellulose, on the other hand, has been found to be ineffective in combination with PVC).

The resulting membrane may be activated by treating it in a known manner so as to provide a chemical binding agent between it and the enzyme, i.e., between the filler particles and the enzyme. This binding may take place by chemiadsorption, covalent binding, or by cross-linking between the intermediate agent and the enzyme. Included amongst the bonding functionalities which may be imparted to the membrane include any free amino residues, as well as carboxyl, isonitrile, aldehyde, or ketone groups which will bind the S-oxynitrilase enzyme to the membrane filler. Of these, polyethyleneimine (PEI), which may be chemiadsorbed on the filler, is preferred, in combination with, e.g., glutaraldehyde, to which the enzyme is then bound.

As disclosed in U.S. Pat. No. 4,102,746 (above), the membrane used in the process of this invention may readily be prepared by admixing suitable quantities of a finely divided polymeric resin, a finely divided inorganic filler, a solvent (e.g., cyclohexanone) and a non-solvent (e.g., water) under low shear conditions to form a stable, damp, free-flowing powder. The powder mixture may then be extruded and calendered preferably to form a substantially planar structure or sheet of desired dimensions which may next be passed through an aqueous bath to leach out the solvent, and then subsequently passed through a heated air-oven to remove the water. In accordance with the present invention, the resulting article in the form of a microporous, dimensionally stable, semi-rigid, insoluble, fluid permeable membrane may then be treated in such a manner as to couple or bond enzymes thereto.

In one preferred, but non-limiting embodiment, the initial, non-chemically activated membrane may be prepared in the following manner: a sheet of porous material is prepared by first dry blending 20.0 lbs. of Conoco TM 5385 poly(vinyl chloride) resin having a particle size of about 80 mesh, and 40.0 lbs. of Hi Sil TM 233, a precipitated hydrated silica, in a Patterson Kelley "low shear" liquids-solids blender for approximately 3 minutes. Thereafter, and during continued agitation, 54.6 lbs. of solvent (cyclohexanone) are added over a 20 minute period by means of a pump. Water in an amount of 59.0 lbs. is then added to the mix in the agitating blender over a subsequent 20-minute period to form a damp, stable, free-flowing powder. The powder is then introduced into a screw extruder having a barrel temperature of approximately 120° F., and the extrudate passed between the rolls of a calender to obtain a substantially flat sheet having a thickness of 0.02 inches (0.5mm). The sheet is then passed through an extraction bath of water at 170° F. and subsequently dried in a hot air oven at 225° F. for 6 minutes. The finished porous sheet has a relatively wide pore size distribution extending from about 0.01 micron to about 100 micron and a mean pore diameter in the range of about 0.15 micron to about 0.25 micron as determined by the Mercury Intrusion method. The total porosity of this material is approximately 65% by volume, and the dispersed filler content (e.g., silica) comprises approximately 56% by weight. In a routine test, e.g., liquid water will soak rapidly into the material without any applied pressure, indicating that the micropores are substantially interconnected from surface to surface.

The above-prepared membrane may then be chemically modified with a binding agent, if desired, to more firmly bind the S-oxynitrilase, by the following means: the untreated membrane is incubated in a 5% wt/vol aqueous solution of 50,000 mol. wt. branched chain polyethyleneimine (PEI) at room temperature for one hour. The treated support is flushed with water and 1M NaCl to remove any unadsorbed PEI. Assay may be by a trinitrobenzene sulfonic acid test: an intense orange trinitrophenyl amine derivative is observed on the surface of the treated support member, thus demonstrating substantial aliphatic amino functionality. The nitrogen loading on the treated support member is quantitated by elemental analysis, e.g., 1.25% nitrogen by dry weight versus 0.02% nitrogen by dry weight of an untreated support member. The chemiadsorption of PEI on the treated support member is virtually irreversible, i.e., it can not be removed by incubation with high ionic strength solutions (e.g., 1M NaCl or 1 M $K_2HPO_4/KH_2PO_4$) at pH values between 3 and 9. Only in the case of strong acidic conditions (incubation in 1M HCl for 2 hours) might there be evidence of partial desorption amounting to 50% of the nitrogen content as indicated by elemental analysis. The surface area of the treated support by standard BET procedure is 55.4 $M^2$/g versus 81.1 $M_2$/g for the control. The support member treated with PEI displays identical flow properties compared to an untreated support member irrespective of the buffer or ionic strength used.

The enzyme is then bound to the membrane which has been chemically activated with, first, PEI, as described above, and then with a linking group such as glutaraldehyde to which the enzyme ultimately binds. The reactants are then brought in contact with the enzyme as they flow through the pores of the membrane. The flow of the reaction medium is desirably controlled by supporting the membrane, or layers of membranes, in a housing or holder which, by retaining the edges of the membrane to form a reactor unit, makes these edges impervious to said flow. If desired, inlet and outlet ports having access to the surfaces of the membrane, thereby directing and forcing the reactants through the pores of the reactor core, and in contact with the enzyme, may also be provided. Typical reactors of this type, in the form of disks, include ACTI-DISK ® and ACTI-MOD ®, (FMC Corporation, Philadelphia, Pa., U.S.A.). The latter disk in particular is comprised of several layers of membranes to ensure more complete recovery. Therefore, it will be understood throughout the description that the term "membrane" is understood to include one or more layers of membranes, wherein the final thickness necessary may readily be determined by routine tests. Thus, in the following examples, the ACTI-DISK ® matrix contained anywhere from one to about 5 layers of membranes, e.g., one membrane in Examples 2, 3, 6, and 7, and 5 layers in Examples 1, 4, and 5.

The desired cyanohydrin reaction product may then be recovered by removal of the hydrocyanic acid and solvent by distillation.

The invention will now be illustrated by, but is not intended to be limited to, the following examples.

EXAMPLE 1

Preparation of (S)-(Cyano)(3-Phenoxyphenyl)Methanol from Hydrogen Cyanide and 3-Phenoxybenzaldehyde in Di-n-Butyl Ether at Ambient Temperature

Step A

Immobilization of S-oxynitrilase enzyme on a porous matrix

An ACTI-DISK ® Support Matrix, containing a poly(vinyl chloride) and silica membrane (MPS ® sheets, FMC Corp., Phila., Pa.), and pretreated with polyethyleneimine, was incorporated into a standard pump-around reactor. The reactor consisted of a fluid metering pump, capable of pumping a maximum of 10 mL/minute, connected from its outlet by clear, flexible plastic tubing to the inlet port of the ACTI-DISK Support Matrix, which was, in turn, connected from its outlet port to a 100 mL reservoir. The reservoir was connected by tubing to the inlet of the pump. The ACTI-DISK Support Matrix (Biosupport Materials, Chemical Products Group, FMC Corporation, Philadelphia, Pa.) consisted of a plastic housing, 63.5 mm in diameter and 6.4 mm thick, having an inlet port on one of its flat sides and an outlet port on its opposite flat side. Contained within the plastic housing were five layers of a fluid permeable porous membrane consisting of a hydrophobic polymeric matrix of poly(vinyl chloride), a finely divided hydrophilic filler of silica dispersed throughout the resinous matrix, and a network of interconnected micropores formed throughout the material.

Twenty-five mL of an aqueous 5% (wt/v) glutaraldehyde solution, for the purpose of linking the N-terminus of the enzyme to the PEI-modified ACTI-DISK, was placed in the reservoir and pumped at a rate of 8 mL/minute through the ACTI-DISK Support Matrix for 60 minutes. The solution was replaced with 50 mL of water, and this was pumped through the ACTI-DISK Support Matrix for 30 minutes. The water was then removed from the reservoir.

Twenty-eight mL of an aqueous solution of S-oxynitrilase enzyme obtained from 7-day old etiolated shoots of Sorghum/Sudan grass hybrid (protein analysis: 5.4 mg protein/mL; enzyme activity analysis: 10.7 units/mg protein) was diluted to 100 mL with 0.05M sodium acetate buffer (pH=5.4) solution and placed in the reservoir. The solution was pumped through the ACTI-DISK Support Matrix for 30 minutes. After this time, flow through the ACTI-DISK Support Matrix was reversed in the pump-around reactor to promote complete and uniform loading of the enzyme. Pumping of the enzyme solution was continued for an additional 30 minutes. The ACTI-DISK Support Matrix was then washed with 50 mL of water for 30 minutes as described above. After this time, the housing containing the ACTI-DISK Support Matrix with S-oxynitrilase enzyme immobilized in it was removed from the pump-around reactor and stored in a refrigerator until needed.

Step B

Preparation of (S)-(Cyano)(3-Phenoxyphenyl)Methanol from Hydrogen Cyanide and 3-Phenoxybenzaldehyde in Di-n-Butyl Ether at Ambient Temperature The ACTI-DISK Support Matrix of Step A, containing immobilized enzyme, was incorporated into a standard pump-around reactor. The reservoir in this system had a capacity of 250 mL or more. Residual water was removed from the ACTI-DISK Support Matrix by pumping a small amount of di-n-butyl ether continuously through the ACTI-DISK Support Matrix for a period of about 30 minutes. In a typical batch, the reservoir was charged with a solution of from 5.1 grams (0.026 mole) to 24.8 grams (0.125 mole) of 3-phenoxybenzaldehyde in 100 mL of di-n-butyl ether. To this was added by syringe 1.1 molar equivalents of hydrogen cyanide. The solution was stirred to ensure complete dissolution of the hydrogen cyanide. Circulation of the solution through the ACTI-DISK Support Matrix at a pump rate of from 1 mL/minute to 5 mL/minute was commenced. Samples were taken periodically for analysis as described below. Upon completion of the reaction, (typically after about 24 hours) the reaction mixture was pumped out of the reactor. The ACTI-DISK Support Matrix was then rinsed by pumping 25 mL of di-D-butyl ether through it. Following the rinse, the reactor was in condition to process another batch.

Two analyses were conducted on each sample removed from the reaction mixture. One analysis was conducted to determine the total conversion of 3-phenoxybenzaldehyde to (cyano)(3-phenoxyphenyl)methanol, while the second analysis was conducted to determine the -S/R ratio of the product so prepared.

To determine the conversion to (cyano)(3-phenoxyphenyl)methanol, a 0.1 mL sample of the reaction mixture was placed in a gas chromatography autosampler vial and diluted to about 1 mL with methylene chloride. To this was added about 1 mL of N,O-bis(trimethylsilyl)trifluoroacetamide. The vial was closed and shaken, after which it was allowed to stand for 15 minutes. A sample of the solution was injected into an appropriately programmed gas chromatograph.

To determine the S/R ratio of the (cyano)(3-phenoxyphenyl)methanol, a 0.5 mL sample of the reaction mixture was placed in a 1 dram vial. To this was added three drops of Mosher's acid chloride (S-(−)-α-methoxy-α-(trifluromethyl)phenylacetic acid chloride) and five drops of pyridine. The resultant reaction mixture was mixed and then was allowed to react for one hour. After this time 1 mL of water and 1 mL of ethyl acetate were added to the reaction mixture. The mixture was shaken, and the ethyl acetate layer was removed and placed in a gas chromatography autosampler vial. A sample of the solution was injected into an appropriately programmed gas chromatograph.

Results of a seven-batch process to prepare (S)-(cyano)(3-phenoxyphenyl)methanol are shown below:

| Run | Aldehyde (Moles) | Pump Rates | Run Time | Conversion To Product | S/R Ratio |
|---|---|---|---|---|---|
| 1 | 0.026 | 1 mL/min | 24 hrs | 76.3% | 91.4/8.6 |
| 2 | 0.026 | 5 mL/min | 23 hrs | 91.8% | 91.4/8.6 |
| 3 | 0.026 | 5 mL/min | 19 hrs | 88.4% | 92.4/7.6 |
| 4 | 0.026 | 5 mL/min | 24 hrs | 91.2% | 93.7/6.3 |
| 5 | 0.125 | 5 mL/min | 24 hrs | 94.0% | 91.0/9.0 |
| 6 | 0.125 | 5 mL/min | 24 hrs | 90.7% | 85.7/14.3 |
| 7 | 0.026 | 5 mL/min | 24 hrs | 80.7% | 75.5/24.6 |

EXAMPLE 2

Preparation of (S)-(Cyano)(3-Phenoxyphenyl)Methanol from Hydrogen Cyanide and 3-Phenoxybenzaldehyde in Di-n-Butyl Ether at a Temperature of 6° C.

The (S)-(cyano)(3-phenoxyphenyl)methanol of this example was prepared by the process as described in Example 1. The pump-around reactor differed in that the ACTI-DISK Support Matrix contained only one layer of the fluid permeable microporous member upon which the S-oxynitrilase enzyme was immobilized. The ACTI-DISK Support Matrix used in this process was immersed in a constant temperature bath which was maintained at 6° C. A total of sixteen batches were reacted. Each batch consisted of 1.0 gram (0.005 mole) of 3-phenoxybenzaldehyde and 0.4–0.5 mL (excess) of hydrogen cyanide in 25 ml of di-n-butyl ether. The pump rate was maintained at 4 to 5 mL/minute. Results of a sixteen batch process to prepare (S)-(cyano)3-phenoxyphenyl)methanol are shown below:

| Run | Run Time | Conversion To Product | S/R Ratio |
| --- | --- | --- | --- |
| 8 | 23 hrs | 70.0% | 95.0/5.0 |
| 9 | 26 hrs | 65.8% | 93.2/6.8 |
| 10 | 24 hrs | 62.8% | 94.0/6.0 |
| 11 | 24 hrs | 65.7% | 93.0/7.0 |
| 12 | 27 hrs | 63.9% | 93.0/7.0 |
| 13 | 24 hrs | 65.9% | 93.4/6.6 |
| 14 | 36 hrs | 76.9% | 93.0/7.0 |
| 15 | 24 hrs | 75.0% | 93.5/6.5 |
| 16 | 23 hrs | 78.2% | 95.0/5.0 |
| 17 | 24 hrs | 77.1% | 96.0/4.0 |
| 18 | 23 hrs | 76.4% | 95.0/5.0 |
| 19 | 24 hrs | 72.7% | 94.5/5.5 |
| 20 | 24 hrs | 69.2% | 93.0/7.0 |
| 21 | 24 hrs | 70.2% | 90.0/10.0 |
| 22 | 24 hrs | 68.2% | 87.0/13.0 |
| 23 | 24 hrs | 56.1% | 81.0/19.0 |

EXAMPLE 3

Preparation of (S)-(Cyano)(3-Phenoxyphenyl)Methanol from Hydrogen Cyanide and 3-Phenoxybenzaldehyde in Tert-Butyl Methyl Ether at Ambient Temperature The (S)-(cyano)(3-phenoxyphenyl)methanol of this example was prepared by the process as described in Example 1. The pump-around reactor differed in that the ACTI-DISK Support Matrix contained only one layer of the fluid permeable microporous member upon which the S-oxynitrilase enzyme was immobilized. A total of three batches were reacted. Each batch consisted of 1.0 gram (0.005 mole) of 3-phenoxybenzaldehyde and 0.5 mL of hydrogen cyanide (the latter in excess for purposes of ensuring complete conversion and to compensate for any loss due to evaporation). The solvent for the first batch was 50 mL of di-n-butyl ether and the solvent for the following two batches was 50 mL each of tert-butyl methyl ether. Each batch was reacted for a 24 hour period. The pump rate was maintained at 5 mL/minute. Results of a three batch process to prepare (S)-(cyano)(3-phenoxyphenyl)methanol are shown below:

| Run | Solvent | Conversion To Product | S/R Ratio |
| --- | --- | --- | --- |
| 24 | n-Bu₂O | 95.0% | 93.0/7.0 |
| 25 | t-BuOMe | 74.% | 58.0/42.0 |
| 26 | t-BuOMe | 88.5% | 53.0/47.0 |

EXAMPLE 4

Preparation of (S)-(Cyano)(3-Phenoxyphenyl)Methanol from Hydrogen Cyanide and 3-Phenoxybenzaldehyde in Acetonitrile at Ambient Temperature The (S)-(cyano)(3-phenoxyphenyl)methanol of this example was prepared by the process as described in Example 1. The only batch consisted of 25.0 grams (0.126 mole) of 3-phenoxybenzaldehyde and 6 mL (excess) of hydrogen cyanide in 100 mL of acetonitrile. The reaction was conducted for 24 hours at a pump rate of 5 mL/minute. The conversion to product was 88.0% and the S/R ratio of the product was 52.0/48.0.

EXAMPLE 5

Preparation of (S)-(Cyano)(3-Phenoxyphenyl)Methanol from Hydrogen Cyanide and 3-Phenoxybenzaldehyde in Tetrahydrofuran at Ambient Temperature The (S)-(cyano)(3-phenoxyphenyl)methanol of this example was prepared by the process as described in Example 1. The only batch consisted of 5.0 grams (0.025 mole) of 3-phenoxybenzaldehyde and 1.5 mL (excess) of hydrogen cyanide in 100 mL of tetrahydrofuran. The reaction was conducted for 24 hours at a pump rate of 5 mL/minute. The conversion to product was 82.0% and the S/R ratio of the product was 48.0/52.0.

EXAMPLE 6

Preparation of (S)-(Cyano)(3-Phenoxyphenyl)Methanol from 3-Phenoxybenzaldehyde at Ambient Temperature Using Hydrogen Cyanide as Solvent The (S)-(cyano)(3-phenoxyphenyl)methanol of this example was prepared by a process as described in Example 1. The pump-around reactor differed in that the ACTI-DISK Support Matrix contained only one layer of the fluid permeable microporous member upon which the S-oxynitrilase enzyme was immobilized. The only batch consisted of 1.0 gram (0.005 mole) of 3-phenoxybenzaldehyde in 20 mL of hydrogen cyanide. The reaction was conducted for 24 hours at a pump rate of 5 mL/minute. The conversion to product was 96.7% and the S/R ratio of the product was 58.1/41.9.

EXAMPLE 7

Preparation of (S)-(Cyano)(3-Phenoxyphenyl)Methanol from Hydrogen Cyanide and 3-Phenoxybenzaldehyde in Diisopropyl Ether at Ambient Temperature The following example shows that the solvent diisopropyl ether employed in, e.g., U.S. Pat. No. 4,859,784 (above), is ineffective as a solvent in this process.

The (S)-(cyano)(3-phenoxyphenyl)methanol of this example was prepared by a process as described in Example 1. The pump-around reactor differed in that the ACTI-DISK Support Matrix contained only one layer of the fluid permeable microporous member upon which the S-oxynitrilase enzyme was immobilized. A total of two batches were reacted. Each batch consisted of 2.1 grams (0.011 mole) of 3-phenoxybenzaldehyde and 0.6 mL (excess) of hydrogen cyanide. The solvent for the first batch was 50 mL of di-n-butyl ether and the solvent for the second batch was 50 mL of diisopropyl ether. Prior to its use, 500 mL of diisopropyl ether was purified by passing it through a 2.5 cm × 28 cm column of neutral alumina. The purified diisopropyl ether was stored under a nitrogen atmosphere until ready for use. The pump-around reactor was flushed with 75 mL of the purified diisopropyl ether between batches. Each batch was reacted for a 23–24 hour period. The pump rate was maintained at 5 mL/minute. Results of a two batch process to prepare (S)-(cyano)(3-phenoxyphenyl)methanol are shown below:

| Run | Solvent | Conversion To Product | S/R Ratio |
| --- | --- | --- | --- |
| 27 | n-Bu₂O | 89.5% | 94.0/6.0 |
| 28 | i-Pr₂O | 80.0% | 66.0/34.0 |

We claim:

1. In the process for the preparation of optically active (S)-cyanohydrins by the reaction of an aldehyde with hydrocyanic acid by contacting an organic solvent containing the acid and aldehyde with the enzyme S-oxynitrilase, the improvement wherein the enzyme is chemically bound to an insoluble composite comprising a porous membrane through which the reactants are passed, said porous membrane comprising a polymeric resinous binder having finely divided filler particles dispersed throughout said binder and a network of substantially interconnected pores formed therein, the porous membrane being pervious to the flow of a fluid containing said reactants.

2. In the process according to claim 1 for the preparation of optically active (S)-cyanohydrins by the reaction of an aldehyde with hydrocyanic acid by contacting an organic solvent containing the acid and aldehyde with the enzyme S-oxynitrilase, the improvement wherein the enzyme is chemically bound to an insoluble composite comprising a porous membrane, or layers of membranes, having at least a pair of opposed surfaces and a predetermined thickness, through which the reactants are passed, said porous membrane comprising a polymeric resinous binder having finely divided filler particles dispersed throughout said binder and a network of substantially interconnected pores formed therein, said pores being formed within said resinous binder, between said filler particles and the resinous binder, and between neighboring filler particles, the dispersed filler particles being present in said porous membrane in an amount by weight of at least about 25%, the size distribution of said pores varying non-uniformly across each of said surfaces and across said predetermined thickness through the range of about 0.01 micron to about 100 microns as determined porosimetrically by the Mercury Intrusion Method, the porous membrane being pervious to the flow of a fluid through at least one of said surfaces.

3. The process of claim 1 or 2 wherein the membrane is comprised of a binder of poly(vinyl chloride) and a filler of silica.

4. The process of claim 1 or 2 wherein the membrane is contained by its edges in a housing which prevents liquid flow through the edges.

5. The process of claim 4 wherein the housing is modified with an inlet port having access to one surface of the membrane and an outlet port having access to the opposite surface of the membrane.

6. The process of claim 1 or 2 wherein the membrane is chemically activated with a binding agent for the enzyme.

7. The process of claim 1 or 2 wherein the enzyme is covalently bonded or cross-linked to the binding agent.

8. The process of claim 6 wherein the membrane is chemically activated with polyethyleneimine and glutaraldehyde.

9. The process of claim 1 or 2 wherein the solubility of the aldehyde in water is less than about 2.0 mg/ml.

10. The process of claim 1 or 2 wherein the aldehyde is 3-phenoxybenzaldehyde.

11. The process of claim 1 or 2 wherein the organic solvent is di-n-butylether.

* * * * *